US012605152B2

(12) United States Patent
Sharma et al.

(10) Patent No.: US 12,605,152 B2
(45) Date of Patent: Apr. 21, 2026

(54) MEDICAL SYSTEMS, DEVICES, AND RELATED METHODS

(71) Applicant: Boston Scientific Medical Device Limited, Galway (IE)

(72) Inventors: Deepak Kumar Sharma, Muzaffarnagar (IN); Sharath Kumar G, Kanakapura (IN); Rajivkumar Singh, Thane (IN); Nachiket Vilas Gole, Pune (IN)

(73) Assignee: Boston Scientific Medical Device Limited, Galway (IE)

( * ) Notice: Subject to any disclaimer, the term of this patent is extended or adjusted under 35 U.S.C. 154(b) by 329 days.

(21) Appl. No.: 18/485,407

(22) Filed: Oct. 12, 2023

(65) Prior Publication Data

US 2024/0122770 A1      Apr. 18, 2024

Related U.S. Application Data

(60) Provisional application No. 63/379,781, filed on Oct. 17, 2022.

(51) Int. Cl.
*A61B 17/00*      (2006.01)
*A61B 1/00*      (2006.01)

(52) U.S. Cl.
CPC ...... *A61B 17/0057* (2013.01); *A61B 1/00087* (2013.01); *A61B 1/00101* (2013.01); *A61B 1/00137* (2013.01)

(58) Field of Classification Search
CPC .................. A61F 13/266; A61F 2/0063; A61F 2002/0072; A61F 2013/2014; A61B 1/00087; A61B 1/00101; A61B 1/00137; A61B 2017/00296; A61B 2017/0061;

A61B 2017/00623; A61B 2017/00818; A61B 2017/00867; A61B 2017/00884; A61B 2017/00893; A61B 2017/00907; A61B 2017/00951; A61B 2017/12004; A61B 2090/0811; A61B 17/005; A61B 17/0057; A61B 2017/00575;
(Continued)

(56) References Cited

U.S. PATENT DOCUMENTS

2021/0162185 A1      6/2021      Smith et al.
2021/0401416 A1      12/2021      King

FOREIGN PATENT DOCUMENTS

WO      WO-2023250167 A1 *   12/2023   ......... A61B 17/0057

* cited by examiner

*Primary Examiner* — Katherine M Shi
(74) *Attorney, Agent, or Firm* — Bookoff McAndrews PLLC

(57)      ABSTRACT

A medical device includes a handle with a primary actuator and one or more secondary actuators, an end cap configured to be coupled to a distal end of another medical device and including stationary and movable portions, one or more patches that are coupled to the movable portion, one or more control elements coupling the primary actuator to the movable portion; and one or more actuation elements. The one or more actuation elements extend from the one or more secondary actuators to a position between a portion of the one or more patches and the movable portion of the end cap. Movement of the primary actuator moves the movable portion of the end cap relative to the stationary portion of the end cap, and movement of the one or more secondary actuators at least partially deploys the one or more patches from the movable portion of the end cap.

20 Claims, 4 Drawing Sheets

(58) Field of Classification Search
CPC ........... A61B 2017/00592; A61B 2017/00597;
A61B 2017/00637; A61B 17/00491;
A61B 2017/0065; A61B 2017/00659
See application file for complete search history.

MEDICAL SYSTEMS, DEVICES, AND RELATED METHODS

CROSS-REFERENCE TO RELATED APPLICATIONS

This application claims the benefit of priority under 35 U.S.C. § 119 from U.S. Provisional Application No. 63/379,781, filed Oct. 17, 2022, which is incorporated by reference herein in its entirety.

TECHNICAL FIELD

The disclosure relates generally to systems, devices, and methods for delivering patches. More specifically, aspects of the disclosure pertain to systems, devices, and/or methods for delivering patches, for example, for hemostasis, via medical devices, such as endoscopes.

BACKGROUND

Bleeding ulcers, for example, in a subject's gastrointestinal (GI) tract, are often difficult to manage and/or provide hemostasis. For example, common treatments for bleeding ulcers include injection therapies, thermal therapies, mechanical therapies, and hemostatic powders. Such therapies are often expensive and/or time-consuming. Furthermore, such therapies may not be able to treat a larger surface area, for example, a larger ulcer in the GI tract. Additionally, a common treatment for chronic ulcers is a gastric bypass. Such procedures may be more difficult, more time-consuming, more costly, and/or less effective/accurate than a minimally-invasive procedure to position a patch on one or more ulcers. Therefore, a need exists for systems, devices, and/or methods for positioning and/or deploying one or more hemostatic patches with one or more portions of a subject.

SUMMARY

This disclosure includes medical systems and devices comprising a biocompatible patch and methods of use thereof, e.g., methods of delivering a patch to a target site of a subject, for example, to help heal an ulcer and/or to perform hemostasis. Each of the aspects disclosed herein may include one or more of the features described in connection with any of the other disclosed aspects.

In one or more examples, a medical device may include a handle, an end cap, one or more patches, one or more control elements, and one or more actuation elements. The handle may include a primary actuator and one or more secondary actuators. The end cap may be configured to be coupled to a distal end of another medical device, and the end cap may include a stationary portion and a movable portion. The one or more patches may be coupled to the movable portion of the end cap. The one or more control elements may couple the primary actuator to the movable portion of the end cap. The one or more actuation elements may extend from the one or more secondary actuators to a position between a portion of the one or more patches and the movable portion of the end cap. Movement of the primary actuator may move the movable portion of the end cap relative to the stationary portion of the end cap. Movement of the one or more secondary actuators may at least partially deploy the one or more patches from the movable portion of the end cap.

The medical device may include one or more of the following features. The one or more secondary actuators may be movably positioned within one or more channels in the primary actuator. The handle may include a handle body. Both the primary actuator and the one or more secondary actuators may be movable relative to the handle body to control the movement of the one or more control elements and the one or more actuation elements. The handle body may include a lumen through which the primary actuator and the one or more secondary actuators are movable. The primary actuator may include a proximal face that is larger than a proximal opening of the lumen of the handle body. Each of the one or more secondary actuators may include a marking or protrusion configured to interact with the handle body at a position corresponding to a deployment of the one or more patches.

The medical device may further include one or more sheath elements. The one or more actuation elements may be positioned within a corresponding one of the one or more control elements. The one or more control elements may be positioned within a corresponding one of the one or more sheath elements. The stationary portion of the end cap may include one or more first through-holes. The one or more sheath elements may be coupled to the stationary portion of the end cap adjacent to a corresponding one of the one or more first through-holes of the stationary portion of the end cap. The at least one control element and the at least one actuation element may extend through the corresponding one of the one or more first through-holes of the stationary portion of the end cap. The movable portion of the end cap may include a proximal ring at a proximal end. The proximal ring may include one or more second through-holes. The one or more control elements may be coupled to the movable portion of the end cap adjacent to a corresponding one of the one or more second through-holes of the proximal ring. The at least one actuation element may extend through the corresponding one of the one or more second through-holes of the proximal ring. The movable portion of the end cap may further include a distal ring at a distal end. The one or more patches may be positioned between the proximal ring and the distal ring. The proximal ring may include a proximal groove. The distal ring may include a distal groove. A portion of the one or more patches may be positioned in the proximal groove. Another portion of the one or more patches may be positioned in the distal groove. A distal portion of the one or more actuation elements may be positioned within the distal groove. The one or more actuation elements may be formed of one or more wires. The one or more control elements may be formed of one or more coils or one or more tubes.

At least a portion of the end cap may be transparent. The one or more actuation elements may be formed of a shape memory material. The one or more secondary actuators may include four secondary actuators. The one or more control elements may include four control elements. The one or more actuation elements may include four actuation elements. The one or more patches may include four patches.

In another aspect, a medical system may include an endoscope with a distal end and a medical device. The medical device may include a handle, an end cap, one or more patches, one or more control elements, and one or more actuation elements. The handle may include a primary actuator and one or more secondary actuators. The one or more secondary actuators may be movably positioned within one or more channels in the primary actuator. The end cap may be coupled to the distal end of the endoscope. The end cap may include a stationary portion and a movable portion. The movable portion may include a proximal ring and a distal ring. The one or more patches may be coupled to the movable portion of the end cap between the proximal ring and the distal ring. The one or more control elements may couple the primary actuator to the movable portion of the end cap. The one or more actuation elements may extend from the one or more secondary actuators to a position between a portion of the one or more patches and the movable portion of the end cap. Movement of the primary actuator may move the movable portion of the end cap relative to the stationary portion of the end cap and relative to the endoscope. Movement of the one or more secondary actuators may at least partially deploy the one or more patches from the movable portion of the end cap The medical system may include one or more of the following features. The medical system may further include a sheath. The sheath may movably surround one or more portions of the endoscope and the end cap. The proximal ring may include one or more through-holes. The one or more control elements may be coupled to the movable portion of the end cap adjacent to a corresponding one of the one or more through-holes of the proximal ring. The at least one actuation element may extend through the corresponding one of the one or more through-holes of the proximal ring. The proximal ring may include a proximal groove. The distal ring may include a distal groove. A portion of the one or more patches may be positioned in the proximal groove. Another portion of the one or more patches may be positioned in the distal groove. A distal portion of the one or more actuation elements may be positioned within the distal groove.

In yet another aspect, a medical device may include a handle, an end cap, one or more patches, and one or more actuation elements. The handle may include one or more actuators. The end cap may be configured to be coupled to a distal end of another medical device. The end cap may include a proximal ring including a proximal groove, a distal ring including a distal groove, and a body portion between the proximal ring and the distal ring. The one or more patches may be coupled to the end cap such that a portion of each of the one or more patches may be positioned within the proximal groove, and such that another portion of each of the one or more patches may be positioned within the distal groove. The one or more actuation elements may extend from the one or more actuators to a position between a portion of the one or more patches and the body portion of the end cap. A distal portion of each of the one or more actuation elements may be positioned within the distal groove. Movement of the one or more actuators may at least partially deploy the one or more patches from the end cap.

The medical device may include one or more of the following features. The one or more actuators may be secondary actuators. The handle may further include a primary actuator configured to control the position of the end cap relative to the distal end of the another medical device. The secondary actuators may be movable within respective channels formed by one or more wings in the primary actuator.

Any of the examples described herein may have any of these features in any combination.

It may be understood that both the foregoing general description and the following detailed description are exemplary and explanatory only and are not restrictive of the invention, as claimed. As used herein, the terms "comprises," "comprising," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate examples of this disclosure and together with the description, serve to explain the principles of the disclosure.

DETAILED DESCRIPTION

Reference is now made in detail to examples of this disclosure, aspects of which are illustrated in the accompanying drawings. Wherever possible, the same reference numbers will be used throughout the drawings to refer to the same or like parts.

Embodiments of this disclosure seek to improve a user's ability to position and/or deploy a patch within a subject's body during a medical procedure, help reduce the need to remove and reintroduce an endoscope or other medical device into the subject's body, help perform hemostasis within the subject, and reduce overall procedure time, among other aspects.

Figure 1:
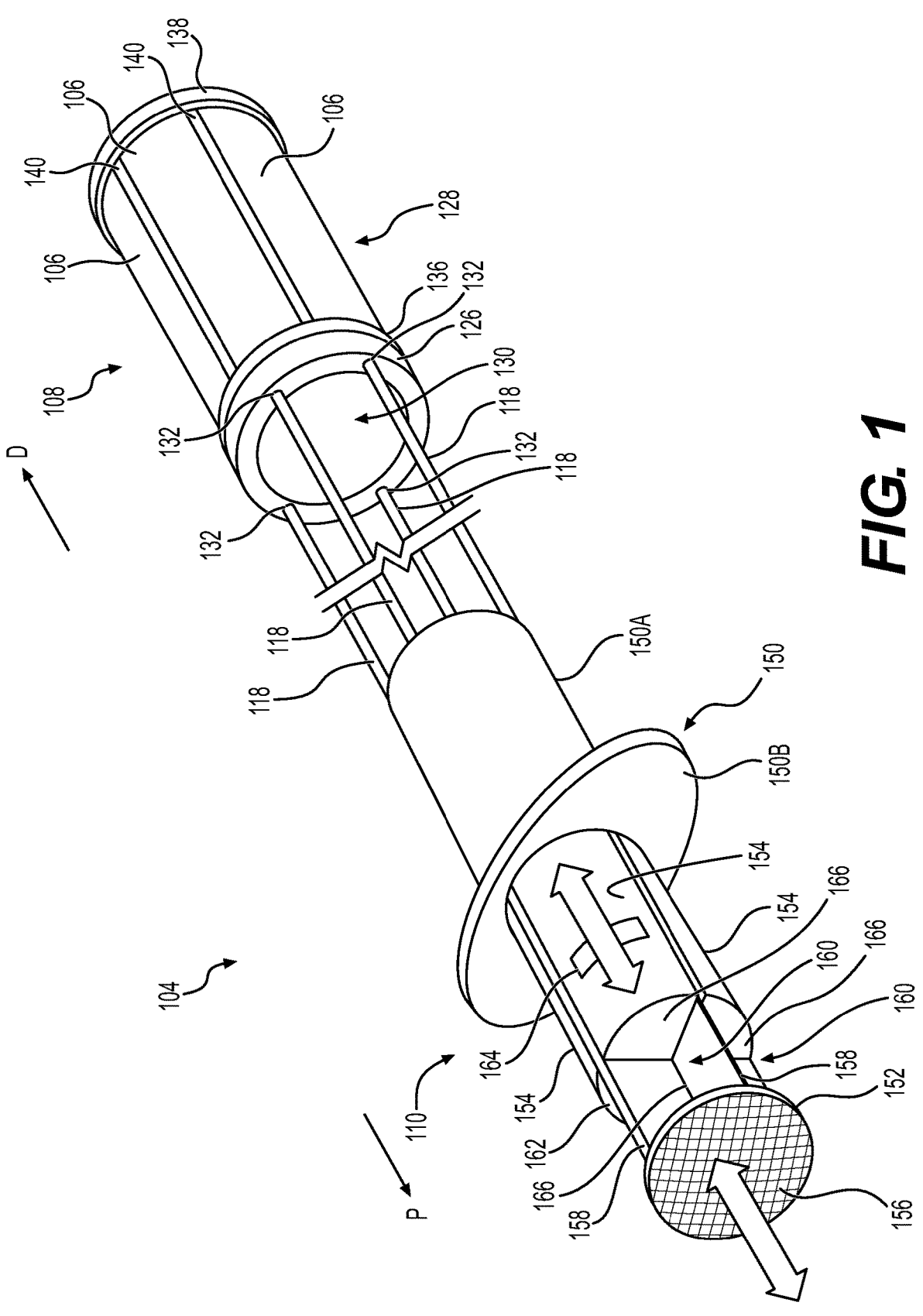
FIG. 1 depicts a perspective view of an exemplary medical device.
Figures 2A, 2B:
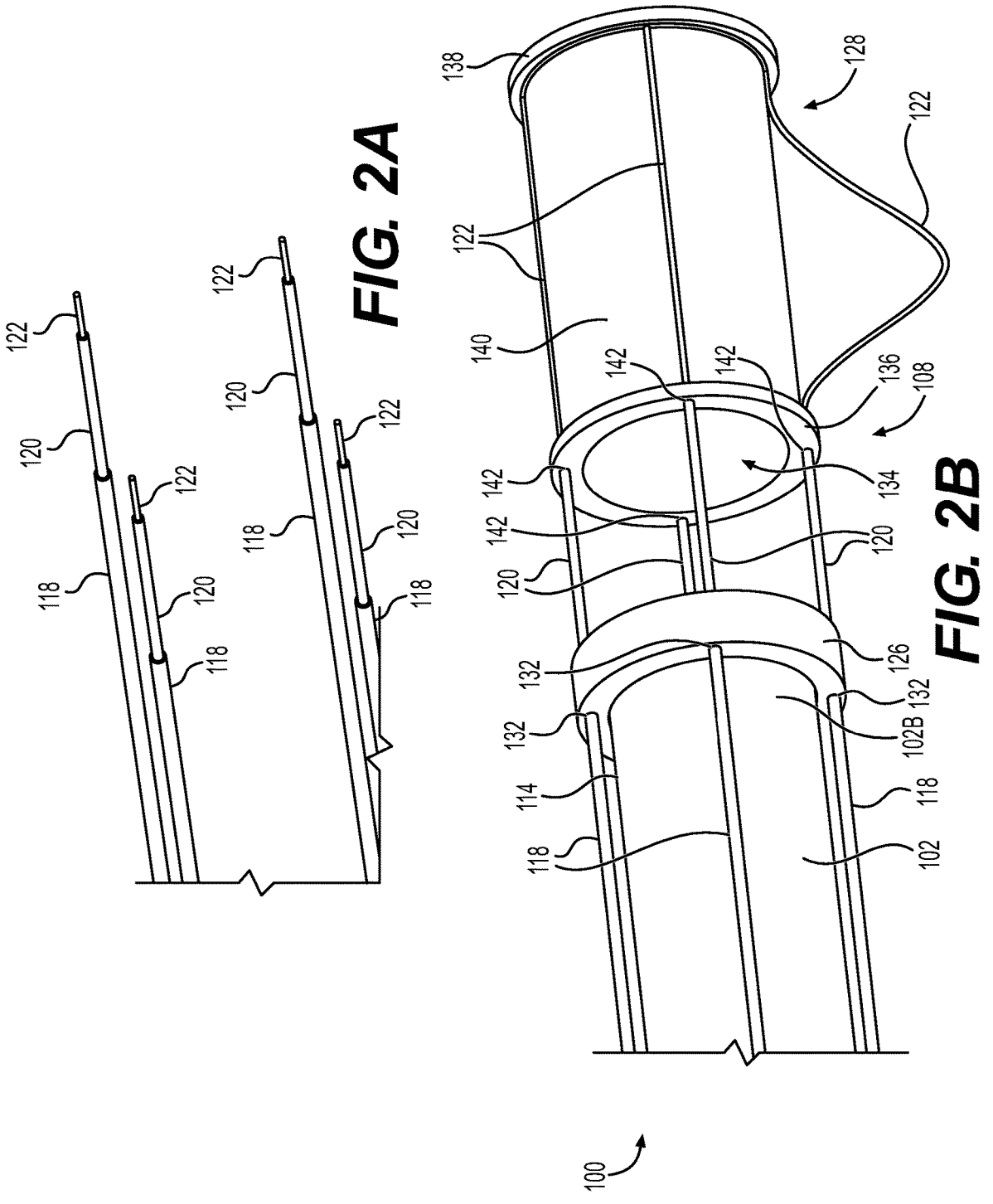
FIG. 2A depicts a perspective view of exemplary control elements.
FIG. 2B depicts a side view of a distal end of the exemplary medical device of FIG. 1, including the exemplary control elements.
Figure 4:
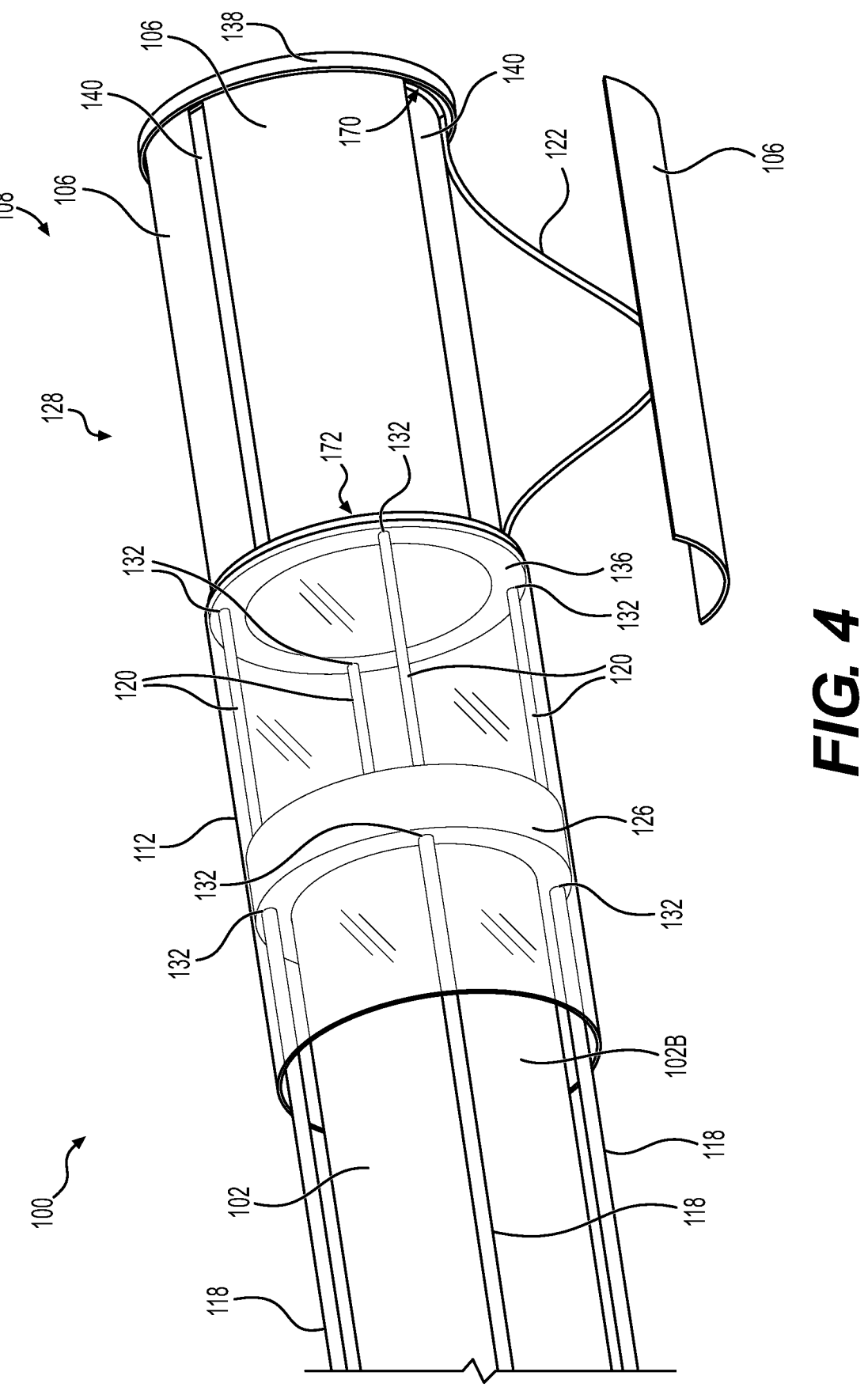
FIG. 4 depicts a perspective view of the distal end of the exemplary medical device of FIG. 1 coupled to an endoscope and in an actuated configuration.

FIG. 1 illustrates a medical device 104. As shown in FIGS. 2B and 4, one or more portions of medical device 104 may be coupled to another or second medical device, for example, an endoscope 102, to form a medical system 100. As discussed in detail herein, medical device 104 may include or otherwise be coupled to a patch delivery system, for example, to position and/or deliver one or more patches 106 to one or more portions of tissue within a subject, which may help perform hemostasis within the subject. Additionally, medical system 100 may include a sheath or other protective element 112 (FIG. 4). Sheath 112 may be movably positioned radially outside of the one or more patches 106, for example, during the delivery of one or more portions of medical system 100 to the treatment site. Sheath 112 may be proximally retracted to expose the one or more patches 106, and one or more portions of medical device 104 may be actuated to position and/or deploy one or more patches 106.

Medical device 104 may be coupled to one or more portions of endoscope 102, for example, in order to deliver one or more portions of medical device 104 to a treatment site. For example, medical device 104 may include an end cap 108. End cap 108 may be coupled a distal portion 102B (i.e., a distal end) of endoscope 102, such that end cap 108 and distal portion 102B of endoscope 102 may be delivered to the treatment site. Furthermore, it is noted that one or more portions, or an entirety, of end cap 108 may be transparent, which may help the user to visualize the treatment site and/or patch 106, for example, with one or more visualization device(s) on endoscope 102.

Medical device 104 may include a handle 110, and manipulation of one or more portions of handle 110 may help to maneuver, position and/or reposition, release or deploy, and/or deliver one or more patches 106, for example, to position one or more patches 106 over tissue at the treatment site. As discussed below, handle 110 may be coupled to end cap 108 via one or more sheath element(s) 118, one or more control element(s) 120, and one or more actuation element(s) 122.

Endoscope 102 may include a generally cylindrical tubular shape, and may include a proximal portion (not shown) and distal portion 102B. Although not shown, the proximal portion may include or otherwise be coupled to a handle, for example, including one or more ports, controls, levers, electrical or communication connections, etc. Additionally, endoscope 102 may include one or more internal lumens or working channels, for example, extending longitudinally through endoscope 102. In these aspects, the internal lumens or working channels may extend through the proximal portion and distal portion 102B, for example, terminating distally at one or more distal openings (i.e., in a distal most end of endoscope 102). As shown in FIG. 1, when medical device 104, including patch 106, is coupled to endoscope 102 (i.e., during the delivery and positioning), patch 106 and a distal portion of medical device 104 may be coupled to distal portion 102B of endoscope 102, for example, coupled to and/or extending distally beyond the distal opening(s) of the internal lumen(s).

Endoscope 102 (i.e., distal portion 102B of endoscope 102) may include a diameter of approximately 9 mm to approximately 15 mm, for example, approximately 10.5 mm to approximately 12 mm. One or more portions of end cap 108 may include a size and/or shape configured to be coupled to (e.g., radially surround) distal portion 102B of endoscope 102. As mentioned, endoscope 102 may include one or more internal lumens, for example, a working channel with a diameter of approximately 2 mm to approximately 4 mm, for example, approximately 2.8 mm. Additionally, endoscope 102, for example, a distal end face (not shown) of endoscope 102, may include one or more illumination device(s) (e.g., one or more LEDs, optical fibers, and/or other illuminators) and/or one or more visualization device(s) (e.g., one or more cameras, one or more image sensors, endoscopic viewing elements, optical assemblies including one or more image sensors and one or more lenses, etc.).

Although not shown, endoscope 102 may include one or more grooves, channels, lumens, or other features to movably receive one or more of control element(s) 120, actuation element(s) 122, and/or sheath element(s) 124. Furthermore, although not shown, one or more portions of endoscope 102 (i.e., distal portion 102B) may be deflectable, for example, via one or more knobs or other controls on a proximal handle. In these aspects, distal portion 102B of endoscope 102 may be maneuvered while being delivered to the treatment site and/or positioned relative to the treatment site, for example, in a retroflex position, which may be used when the treatment site is in the subject's esophagus, stomach, duodenum, colon, or other portion of the GI tract.

Although the treatment site is discussed as being in the subject's GI tract, this disclosure is not so limited, as the treatment site may be any internal lumen or other tissue within the subject. Additionally, although endoscopes are referenced herein, it will be appreciated that the disclosure encompasses any medical devices having a working channel extending from a proximal end to a distal end, such as ureteroscopes, duodenoscopes, gastroscopes, endoscopic ultrasonography ("EUS") scopes, colonoscopes, bronchoscopes, laparoscopes, arthroscopes, cystoscopes, aspiration scopes, sheaths, or catheters.

Additionally, in some aspects, medical system 100 may include sheath 112, for example, an outer sheath (FIG. 4). Sheath 112 may be movable and may surround one or more portions of endoscope 102 and medical device 104, for example, during the delivery of endoscope 102 (distal portion 102B) and end cap 108 to the treatment site. Sheath 112 may help to cover one or more patches 106 during the delivery of endoscope 102 and end cap 108 to the treatment site. For example, as shown in FIG. 4, sheath 112 may be proximally retracted once endoscope 102 and end cap 108 are positioned at the treatment site, exposing one or more patches 106.

Patch 106 may be a biodegradable and/or biocompatible patch of any suitable shape and any suitable dimension, e.g. based on the nature of the target tissue site. Patch 106 may be flexible and may have any shape such as, e.g., approximately square, approximately rectangular, rounded square, rounded rectangle, ovate, circular, among other possible shapes. In some examples, the thickness of the patch may be on the order of millimeters, e.g. ranging from approximately 0.1 mm to approximately 5.0 mm or, more specifically, from approximately 0.7 mm to approximately 2.0 mm. Patch 106 may be sufficiently sized to cover the target tissue with a margin for resection. Thus, patch 106 can come in many sizes to accomplish such a task. In some aspects, patch 106 may be approximately 50 mm by 50 mm (i.e., approximately 2 inches by 2 inches).

Patch 106 may be of any suitable color, including clear. Patch 106 may be formed of any suitable material, e.g., nettings, meshes, cloths, gelatins, or polysaccharides (chitosan, cellulose, starch, alginates, etc.) that may be further modified with synthetic biocompatible materials (pHEMA, PGA, PLA, PCA, PEG, etc.). In some aspects, patch 106 may be formed of a bioadhesive material, for example, such as chitosan, modified chitosan, cellulose, pHEMA, PVA, PEG, or composites of one or more of these polymers. Additionally, for example, patch 106 may be comprised of polypropylene, polyester, Polytetrafluoroethylene (PTFE), expanded Polytetrafluoroethylene (ePTFE), and/or silicone. Patch 106 may be adhered to the target tissue using materials commonly known in the art, such as, for example, fibrin glue, hydrogel, and/or cyanoacrylate. Alternatively or additionally, patch 106 may be comprised of and/or dosed with agents to prevent the shedding of cells from the target tissue or to treat the target site. In some aspects, patch 106 may include a treatment agent, for example, an antibiotic and/or hemostatic agent. Moreover, after patch 106 is delivered to the treatment site, the user may spray, apply, or otherwise deliver one or more hemostatic agents (e.g., one or more hemostatic powders), for example, through a working channel (e.g., an internal lumen) of endoscope 102 or another medical device.

As shown in FIG. 1, medical device 104 includes end cap 108 and handle 110. One or more sheath elements 118 may extend between handle 110 and end cap 108, for example, from one or more portions of handle 110 to one or more portions of end cap 108. Sheath element(s) 118 may each be formed by a coil, a tube, a sheath, etc. Additionally, one or more control elements 120 and one or more actuation elements 122 may extend from one or more portions of handle 110 to one or more portions of end cap 108. Control element(s) 120 may each be formed by a coil, a tube, a sheath, etc. Actuation element(s) 122 may each be formed by a wire, a coil, a tube, a rod, etc. In these aspects, as shown in FIG. 2A, each control element 120 may be radially within a respective sheath element 118. Moreover, each actuation element 122 may be radially within a respective control element 120.

As shown in FIGS. 1 and 2B, end cap 108 may include a stationary portion 126 and a scaffold or a movable portion 128. FIG. 2B illustrates end cap 108 without one or more patches 106, in order to illustrate internal features of end cap 108. Stationary portion 126 may be coupled to distal portion 102B of endoscope 102 (FIG. 2B). Stationary portion 126 may be cylindrical and/or ring-shaped with a lumen 130 extending longitudinally through stationary portion 126. Stationary portion 126 may be configured to be coupled to a radially-outward facing surface or outer surface 114 of endoscope 102 (FIG. 2B). Stationary portion 126 may be coupled to distal portion 102B of endoscope 102, for example, via a friction fit, an adhesive, a press fit, a crimping, or any other appropriate coupling mechanism.

Moreover, stationary portion 126 may include one or more through-holes 132 extending longitudinally through portions of stationary portion 126 (i.e., radially outward of lumen 130). In some aspects, each of sheath element(s) 118 may be coupled to a corresponding through-hole 132. Additionally, control element(s) 120 (and actuation element(s) 122) may extend longitudinally through a corresponding through-hole 132. In these aspects, control element(s) 120 (and actuation element(s) 122) may move longitudinally (i.e., proximally and/or distally) relative to stationary portion 126 through corresponding through-holes 132, for example, to control a position of movable portion 128 relative to stationary portion 126 and/or to endoscope 102 (FIG. 2B)

Although not shown, stationary portion 126 (and/or movable portion 128) may include one or more radiopaque markers, protrusions, or indicators. The one or more radiopaque markers, protrusions, or indicators may be, for example, configured to facilitate visualization of stationary portion 126 (and/or movable portion 128), for example, via X-ray, CT scan, etc. or other external visualization techniques.

Movable portion 128 may be generally cylindrical, and may include a lumen 134 (FIG. 2B) extending longitudinally through movable portion 128. Moreover, movable portion 128 may include a proximal ring 136 and a distal ring 138. Proximal ring 136 and distal ring 138 may each extend radially away from a body portion 140 of movable portion 128. For example, proximal ring 136 and distal ring 138 may include larger thicknesses or radial widths than body portion 140 of movable portion 128. In these aspects, as shown in FIG. 1 and as discussed in detail with respect to FIGS. 3A-3C, one or more patches 106 may be positioned between proximal ring 136 and distal ring 138.

Additionally, movable portion 128 may include one or more through-holes 142 extending longitudinally through portions of movable portion 128 (i.e., radially outward of lumen 130). In some aspects, each of control element(s) 120 may be coupled to a corresponding through-hole 142. Additionally, actuation element(s) 122 may extend longitudinally through a corresponding through-hole 142. Distal ends of actuation element(s) 122 may be coupled to or otherwise abut distal ring 138. In these aspects and as described in detail below, movement of control element(s) 120, for example, via one or more actions on handle 110, may control the position of movable portion 128 relative to stationary portion 126 and/or to distal portion 102B of endoscope 102. Moreover, movement of actuation element(s) 122, for example, via one or more different actions on handle 110, may control the position and/or deployment of one or more patches 106.

As mentioned above, handle 110 may be coupled to end cap 108 via sheath element(s) 118, control element(s) 120, and/or actuation element(s) 122. Additionally, referring to FIG. 1, handle 110 may include a handle body 150, which includes an internal lumen (not shown). In some aspects, proximal ends of sheath element(s) 118 may be coupled to a distal end or distal portion of handle body 150. Handle body 150 may include a main body portion 150A, which may be generally tubular or cylindrical (as shown) or may be another appropriate shape. Main body portion 150A may be configured to be held in user's handle and/or between fingers. Handle body 150 may also include an extension portion 150B, for example, extending radially outward from a proximal end of main body portion 150A. In some aspects, extension portion 150B may be generally ovular. Although not shown, extension portion 150B may be circular, rectangular, or another appropriate shape. Main body portion 150A and extension portion 150B may help the user to grip handle body 150, for example, with one hand, while also allowing the user to actuate or otherwise manipulate one or more other portions handle 110, for example, with the same one hand.

Furthermore, in some aspects, handle 110 includes a primary actuator 152 and one or more secondary buttons or actuators 154. Primary actuator 152 and one or more secondary actuators 154 may be movable within the internal lumen of handle body 150. Primary actuator 152 may be coupled to control element(s) 120. For example, a distal portion of primary actuator 152 may be coupled to proximal ends of control element(s) 120, for example, within the internal lumen of handle body 150. The distal portion of primary actuator 152 may be coupled to proximal ends of control element(s) 120, for example, via a friction fit, an adhesive, a press fit, a crimping, or any other appropriate coupling mechanism. In this aspect, movement (i.e., proximal or distal movement) of primary actuator 152 relative to handle body 150 may control the extension or retraction of control element(s) 120 relative to sheath element(s) 118, and thus control the extension or retraction movable portion 128 relative to stationary portion 126 (FIG. 2B).

Additionally, one or more secondary actuators 154 may be coupled to actuation element(s) 122. For example, a distal portion of each secondary actuator 154 may be coupled to a proximal end of a corresponding actuation element 122, for example, within the internal lumen of handle body 150. The distal portion of each secondary actuator 154 may be coupled to the proximal end of a corresponding actuation element 122, for example, via a friction fit, an adhesive, a press fit, a crimping, or any other appropriate coupling mechanism. In this aspect, movement (i.e., proximal or distal movement) of each secondary actuator 154 relative to handle body 150 may control the extension or retraction of actuation element(s) 122 relative to control element(s) 120, and thus control the position and/or deployment of one or more patches 106.

In these aspects, end cap 108 may include a plurality of patches 106. For example, end cap 108 may include four patches 106 spaced circumferentially around body portion 140 of movable portion 128. Alternatively, end cap 108 may include one, two, three, five, six, seven, eight, etc. patches 106. Patches 106 may be evenly or unevenly spaced around body portion 140 of movably portion 128. Handle 110 may include a number of secondary actuators 154 corresponding to the number of patches 106 on end cap 108. As mentioned, medical device 104 may include a number of sheath elements 118, control elements 120, and actuation elements 122 corresponding to the number of patches 106. Furthermore, medical device 104 may include twice as many (or more) sheath elements 118, control elements 120, and actuation elements 122 corresponding to the number of patches 106. In this manner, two (or more) actuation elements 122 may control the position and/or deployment of a corresponding patch 106.

Moreover, although not shown, handle 110 may include one or more springs or biasing elements, for example, within the internal lumen of handle body 150, to bias the movement of one or more of primary actuator 152 and/or secondary actuator(s) 154. For example, the one or more springs or biasing elements may proximally bias the movement of one or more of primary actuator 152 and/or secondary actuator(s) 154. In these aspects, the user may distally advance one or more of primary actuator 152 and/or secondary actuator(s) 154 relative to handle body 150, but once the distal pressure from the user is removed, the one or more biasing elements may urge one or more of primary actuator 152 and/or secondary actuator(s) 154 proximally. Additionally or alternatively, one or more portions of handle 110 may include a locking mechanism, for example, to selectively and/or releasably secure a position of one or more of primary actuator 152 and/or secondary actuator(s) 154.

Primary actuator 152 may include a proximal face 156. Proximal face 156 may be flat, for example, perpendicular to the longitudinal axis of handle 110 and/or the longitudinal axis of medical device 104. Additionally, proximal face 156 may include a textured surface, which may help the user manipulate primary actuator 152. In some aspects, proximal face 156 may include a size (e.g., diameter or circumference) that is larger than the internal lumen of handle body 150. For example, proximal face 156 may help to control and/or limit the movement (e.g., extension) of movable portion 128 relative to stationary portion 126.

Primary actuator 152 may also include one or more radial extensions or wings 158 (e.g., in an intermediate portion of primary actuator 152), for example, forming one or more channels 160. For example, a plurality of wings 158 may extend radially away from a central portion 162 of primary actuator 152. Outer portions of wings 158 may be angularly or circumferentially spaced apart from adjacent wings 158, forming channels 160. For example, in one aspect, primary actuator 152 may include four wings 158, spaced apart by approximately 90 degrees circumferentially, and forming four channels 160. In these aspects, each of channels 160 may be sized and/or shaped to movably receive one of secondary actuator(s) 154. For example, each of secondary actuator(s) 154 may be wedge shaped, and each of channels 160 may be formed by two wings 158 spaced approximately 90 degrees apart.

As mentioned, handle 110 may include one secondary actuator 154 for each actuation element 122. For example, if medical device 104 includes four actuation elements 122 (as shown), handle 110 may include four secondary actuators 154, with each secondary actuator 154 coupled to a corresponding actuation element 122. For example, a distal end of each secondary actuator 154 may be coupled to a proximal end of a corresponding actuation element 122, for example, within an internal portion of handle body 150. Each secondary actuator 154 may include a proximal face 166. Proximal face 166 may be flat, for example, perpendicular to the longitudinal axis of handle 110 and/or the longitudinal axis of medical device 104. Additionally, proximal face 166 may include a textured surface, which may help the user manipulate secondary actuator(s) 154.

Each of secondary actuators 154 may include different colors, patterns, indications (e.g., letters, numbers, symbols, etc.), which may help the user differentiate between different secondary actuators 154. Furthermore, although not shown, one or more of patches 106 or one or more portions of end cap 108 may include a corresponding color, pattern, indication (e.g., letter, number, symbol, etc.), which may be visible via the visualization element on endoscope 102, a separate internal or external visualization element, etc. In these aspects, the user may correlate which secondary actuator 154 to actuate or otherwise manipulate in order to position and/or deploy the appropriate patch 106.

Moreover, as shown in FIG. 1, one or more of secondary actuators 154 may include one or more projections and/or markings 164. For example, the one or more projections and/or markings 164 may indicate to a user when one or more secondary actuators 154 are in a position corresponding to the extension of actuation element(s) 122 to deploy one or more patches 106. In some examples, one or more projections and/or markings 164 may interact with handle body 150 (e.g., a ridge or bump that may require additional proximal force on secondary actuator(s) 154 to overcome) and/or provide an audible click when secondary actuator(s) 154 have reached a position that will deploy patch 106. In other examples, one or more projections and/or markings 164 may signal or otherwise indicate to a user that actuation element(s) 122 have reached a position that will deploy patch 106 when one or more projections and/or markings 164 on secondary actuator 154 is aligned with or distally within the proximal end of handle body 150. In some examples, although not shown, handle body 150 may include a recess portion configured to receive one or more projections and/or markings 164. In this example, the one or more projections and/or markings 164 may snap or otherwise fit into the recess portion when secondary actuator(s) 154 is in a position relative to handle body 150 such that actuation element(s) 122 has reached a position that will deploy patch 106.

Figures 3A, 3B, 3C:
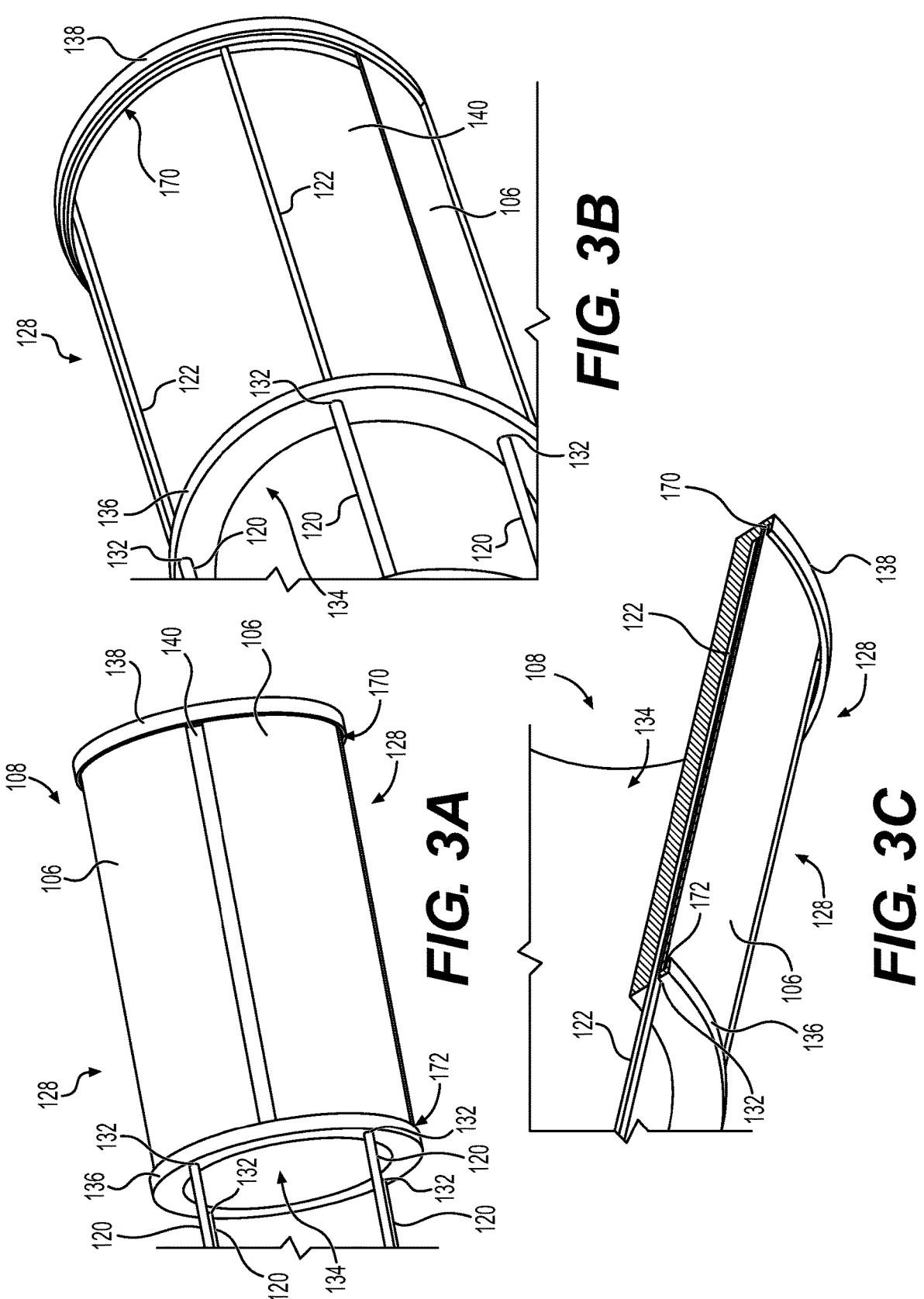
FIGS. 3A-3C depict perspective or cross-sectional views of portions of the distal end of the exemplary medical device of FIG. 1.

FIGS. 3A-3C illustrate additional features of movable portion 128 of end cap 108. FIGS. 3A and 3B are different perspective views of movable portion 128 extended from stationary portion 126 (not shown), and FIG. 3C is a longitudinal cross-sectional view of movable portion 128. As mentioned, movable portion 128 includes one or more through-holes 132, for example, coupled to control elements 120 and to movably receive actuation elements 122. Additionally, movable portion 128 includes lumen 134. Moreover, one or more patches 106 may be positioned between proximal ring 136 and distal ring 138, for example, such that the one or more patches 106 are radially exterior of and/or adjacent to body portion 140.

As shown in FIGS. 3A-3C, distal ring 138 may include a distal groove 170. Additionally, in some aspects and as shown in FIGS. 3A and 3C, proximal ring 136 may include a proximal groove 172. As shown in the cross-sectional view, distal groove 170 and/or proximal groove 172 may extend parallel to a longitudinal axis of movable portion 128, for example, through respective portions of distal ring 138 and proximal ring 136. In these aspects, distal groove 170 and/or proximal groove 172 may extend circumferentially about the longitudinal axis of movable portion 128, for example, through respective portions of distal ring 138 and proximal ring 136. For example, distal groove 170 may extend distally through a proximal face of distal ring 138.

Similarly, proximal groove 172 may extend proximally through a distal face of proximal ring 136. Additionally, distal portions of one or more patches 106 may be positioned within distal groove 170, and proximal portions of one or more patches 106 may be positioned within proximal groove 172. In these aspects, grooves 170, 172 may help to retain one or more patches 106, for example, during the delivery and/or positioning of the one or more patches 106.

Additionally, as shown in FIGS. 3B and 3C, actuation element(s) 122 may extend radially within the one or more patches 106. It is noted that only one patch 106 is shown in FIG. 3B and that control element(s) 120 are omitted in FIG. 3C for clarity. For example, actuation element(s) 122 may extend through a respective through-hole 132 (e.g., in proximal ring 136) and terminate within distal groove 170. A respective actuation element 122 may extend radially within a middle or central portion of a respective patch 106.

FIG. 4 illustrates the movement of movable portion 128 of end cap 108 relative to stationary portion 126 and distal portion 102B of endoscope, and also illustrates the positioning and deployment of patch 106. During operation, a user may first couple medical device 104 to an insertion device, such as endoscope 102, for example, by coupling end cap 108 to distal portion 102B of endoscope 102. The user may then maneuver endoscope 102, using one or more visualization devices, illumination devices, etc. (not shown) at a distal tip of endoscope 102, to navigate to a treatment site within a body of a subject.

As shown, once distal portion 102B of endoscope 102 and end cap 108 are positioned at the treatment site, the user may proximally retract sheath 112, for example, to expose movable portion 128 and the one or more patches 106 coupled to movable portion 128. It is noted that sheath 112 may extend proximally, for example, to handle 110, a proximal end of endoscope 102, etc., but that only a portion of sheath 112 is shown in FIG. 4 for clarity. Alternatively or additionally, movable portion 128 may be extended from stationary portion 126. As mentioned above, the user may manipulate (e.g., distally advance) primary actuator 152 (FIG. 1) to extend movable portion 128. For example, manipulation of primary actuator 152 may distally advance control elements 120 to distally advance movable portion 128. Control elements 120 may move relative to sheath elements 118 and through stationary portion 126, for example, through a respective through-hole 132. Primary actuator 152 may be moved further distally and/or retracted proximally in order to reposition movable portion 128 relative to the treatment site. In some aspects, endoscope 102 may include one or more visualization devices (not shown), which may help the user visualize the treatment site and/or the position of movable portion 128 relative to endoscope 102 and/or the treatment site. Once movable portion 128 is positioned relative to endoscope 102 and/or the treatment site, the user may lock the position of primary actuator 152.

With movable portion 128 positioned, the user may manipulate (e.g., distally advance one secondary actuator 154 (FIG. 1) to advance a selected actuation element 122. For example, the user may select one of the secondary actuators 154 to control the positioning and/or deployment of one patch 106. As shown in FIG. 4, a distal end of actuation element 122 is secured or otherwise positioned within distal groove 170. Moreover, the position of movable portion 128 may be fixed, for example, with the user's hand or finger on primary actuator 152, via one or more locking mechanisms, a frictional engagement with handle body 150, etc. As such, when actuation element 122 is distally advanced, a portion of actuation element 122 extends, bows, bends, or otherwise moves radially outward, for example, away from body portion 140 of movable portion 128, as shown in FIG. 4. For example, actuation element(s) 122 may be formed of a shape-memory material (e.g., Nitinol) or a braided wire, such that when actuation elements 122 are extended distally, actuation elements 122 may take the radially outward extended, bowed, or bent configuration.

Because actuation element 122 is positioned radially within or otherwise between body portion 140 and patch 106, the movement of actuation element 122 urges patch 106 radially outward. For example, a first movement of actuation elements 122 may partially extend patch 106 radially outward away from body portion 140 (e.g., at least partially deploying patch 106), for example, with respective portions of patch 106 retained within distal groove 170 and proximal groove 172. Then, additional movement of actuation element 122 (e.g., such that marking 164 aligns with a proximal end of handle body 150) may further extend patch 106 radially outward away from body portion 140, for example, such that respective portions of patch 106 are no longer retained within distal groove 170 and proximal groove 172.

Once patch 106 is deployed and delivered to the treatment site, the user may inspect patch 106 and the treatment site, for example, using one or more visualization devices, illumination devices, etc. of endoscope 102. The user may reposition patch 106, for example, using one or more auxiliary medical devices, such as a grasper or other auxiliary medical device (e.g., delivered to the treatment site through a working channel of endoscope 102). Moreover, the user may apply a hemostatic agent (e.g., a hemostatic powder) to the delivered patch 106, for example, via one or more auxiliary medical devices delivered through a working channel of endoscope 102.

Furthermore, the user may reposition movable portion 128, for example, via movement of primary actuator 152, and may manipulate another secondary actuator 154 to position and/or deploy another patch 106. The other patch 106 may be delivered to the treatment site, for example, adjacent to the first patch to help cover and/or heal a large ulcer. Alternatively or additionally, the other patch 106 may be delivered to another location on the treatment site. The user may repeat these steps as many times as needed to deploy as many patches 106 as needed at the treatment site, and/or to deploy all of the patches 106 on end cap 108. The multiple patches 106 may be deployed to the treatment site without removing medical system 100, including endoscope 102 and end cap 108, from the subject.

Various aspects of medical system 100, for example, medical device 104 with patch 106, end cap 108, and handle 110, may have a low cost and may be disposable (i.e., a single use device). Medical device 104 may be coupled to any type of scope to help deliver one or more patches 106 to a treatment site (e.g., endoscopically), and coupling end cap 108 to the distal end of a scope may be quick and user-friendly. The one or more patches 106 may be positioned on end cap 108 (e.g., radially around body portion 140 movable portion 128). Additionally, sheath 112 and/or distal ring 138 may help to protect the one or more patches 106 from fluids, tissues, materials, etc. during the delivery of endoscope 102 to the treatment site.

Additionally, medical device 104 may allow for one or more patches 106 to be delivered to the treatment site in a minimally invasive procedure (e.g., endoscopically), without having to deliver the one or more patches 106 through a working channel (e.g., an internal lumen) of endoscope 102. In this aspect, the one or more patches 106 may be larger than patches passed through the working channel. Moreover, the one or more patches 106 and end cap 108 may not interfere with the delivery of one or more auxiliary medical device, delivery of fluid, application of suction, etc., which may be done through the working channel.

Furthermore, in some aspects, patch 106 may be positioned and repositioned before being deployed. For example, as discussed, the user may manipulate primary actuator 152 relative to handle body 150 to position and reposition patch 106 via movement of control element(s) 120. The user may also position and reposition distal portion 102B of endoscope 102. This positioning and repositioning may be done under direct visualization, for example, via one or more visualization device(s) on endoscope 102. Because patch 106 is coupled to endoscope 102 via end cap 108, the distal end face of endoscope 102 may be substantially unobstructed. Additionally, in some aspects, the user may lock or otherwise secure the position of primary actuator 152 relative to handle body 150 via one or more handle locking mechanisms.

Once patch 106 is in the desired position, the user may release or deploy patch 106, for example, via movement (e.g., distal movement) of secondary actuator 154 to control the movement of actuation element(s) 122. As discussed, movement (e.g., distal movement) of actuation element(s) 122 may cause actuation element(s) 122 to extend, bow, or bend radially outward, thus may push patch 106 radially outward such that portions of patch 106 are no longer positioned within distal groove 170 and proximal groove 172. Alternatively or additionally, patch 106 may be initially coupled to one or more actuation element(s) 122 (e.g., adhered using a glue, epoxy, or other adhesive(s)). In this aspect, the distal movement of actuation element(s) 122 that causes actuation element(s) 122 to extend, box, or bend radially outward may also overcome the coupling between patch 106 and actuation element(s) 122, thus releasing or deploying patch 106. Moreover, patch 106 may be positioned relative to the treatment site using one or more auxiliary medical devices, and/or the user may inspect the position of patch 106 at the treatment site, for example, via one or more visualization device(s) on endoscope 102. The positioning and deployment of patch 106 (e.g., via primary actuator 152 and secondary actuator 154 of handle 110) may be straightforward and user-friendly, which may allow the user to be a surgical technician, while the physician performs one or more other tasks during the procedure.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising:
   a handle, wherein the handle includes a primary actuator and one or more secondary actuators;
   an end cap configured to be coupled to a distal end of another medical device, wherein the end cap includes a stationary portion and a movable portion;
   one or more patches, wherein the one or more patches are coupled to the movable portion of the end cap;
   one or more control elements coupling the primary actuator to the movable portion of the end cap; and
   one or more actuation elements, wherein the one or more actuation elements extend from the one or more sec-
ondary actuators to a position between a portion of the one or more patches and the movable portion of the end cap,
   wherein movement of the primary actuator moves the movable portion of the end cap relative to the stationary portion of the end cap, and
   wherein movement of the one or more secondary actuators at least partially deploys the one or more patches from the movable portion of the end cap.

2. The medical device of claim 1, wherein the one or more secondary actuators are movably positioned within one or more channels in the primary actuator.

3. The medical device of claim 1, wherein the handle includes a handle body, and wherein both the primary actuator and the one or more secondary actuators are movable relative to the handle body to control the movement of the one or more control elements and the one or more actuation elements.

4. The medical device of claim 3, wherein the handle body includes a lumen through which the primary actuator and the one or more secondary actuators are movable, and wherein the primary actuator includes a proximal face that is larger than a proximal opening of the lumen of the handle body.

5. The medical device of claim 3, wherein each of the one or more secondary actuators includes a marking or protrusion configured to interact with the handle body at a position corresponding to a deployment of the one or more patches.

6. The medical device of claim 1, further comprising one or more sheath elements, wherein the one or more actuation elements are positioned within a corresponding one of the one or more control elements, and wherein the one or more control elements are positioned within a corresponding one of the one or more sheath elements.

7. The medical device of claim 6, wherein the stationary portion of the end cap includes one or more first through-holes, wherein the one or more sheath elements are coupled to the stationary portion of the end cap adjacent to a corresponding one of the one or more first through-holes of the stationary portion of the end cap, and wherein the one or more control elements and the one or more actuation elements extend through the corresponding one of the one or more first through-holes of the stationary portion of the end cap.

8. The medical device of claim 7, wherein the movable portion of the end cap includes a proximal ring at a proximal end of the end cap, wherein the proximal ring includes one or more second through-holes, wherein the one or more control elements are coupled to the movable portion of the end cap adjacent to a corresponding one of the one or more second through-holes of the proximal ring, and wherein the one or more actuation elements extend through the corresponding one of the one or more second through-holes of the proximal ring.

9. The medical device of claim 8, wherein the movable portion of the end cap further includes a distal ring at a distal end of the end cap, and wherein the one or more patches are positioned between the proximal ring and the distal ring.

10. The medical device of claim 9, wherein the proximal ring includes a proximal groove, wherein the distal ring includes a distal groove, wherein a portion of the one or more patches is positioned in the proximal groove, and wherein another portion of the one or more patches is positioned in the distal groove.

11. The medical device of claim 10, wherein a distal portion of the one or more actuation elements is positioned within the distal groove.

12. The medical device of claim 11, wherein the one or more actuation elements are formed of one or more wires, and wherein the one or more control elements are formed of one or more coils or one or more tubes.

13. The medical device of claim 1, wherein at least a portion of the end cap is transparent.

14. The medical device of claim 1, wherein the one or more actuation elements are formed of a shape-memory material.

15. The medical device of claim 1, wherein the one or more secondary actuators includes four secondary actuators, wherein the one or more control elements includes four control elements, wherein the one or more actuation elements includes four actuation elements, and wherein the one or more patches includes four patches.

16. A medical system, comprising:

an endoscope, including a distal end;

a medical device, wherein the medical device includes:

a handle, wherein the handle includes a primary actuator and one or more secondary actuators, wherein the one or more secondary actuators are movably positioned within one or more channels in the primary actuator;

an end cap coupled to the distal end of the endoscope, wherein the end cap includes a stationary portion and a movable portion, and wherein the movable portion includes a proximal ring and a distal ring;

one or more patches, wherein the one or more patches are coupled to the movable portion of the end cap between the proximal ring and the distal ring;

one or more control elements coupling the primary actuator to the movable portion of the end cap; and one or more actuation elements, wherein the one or more actuation elements extend from the one or more secondary actuators to a position between a portion of the one or more patches and the movable portion of the end cap, wherein movement of the primary actuator moves the movable portion of the end cap relative to the stationary portion of the end cap and relative to the endoscope, and wherein movement of the one or more secondary actuators at least partially deploys the one or more patches from the movable portion of the end cap.

17. The medical system of claim 16, further comprising a sheath, wherein the sheath movably surrounds one or more portions of the endoscope and the end cap.

18. The medical system of claim 17, wherein the proximal ring includes one or more through-holes, wherein the one or more control elements are coupled to the movable portion of the end cap adjacent to a corresponding one of the one or more through-holes of the proximal ring, and wherein the one or more actuation elements extend through the corresponding one of the one or more through-holes of the proximal ring, and wherein the proximal ring includes a proximal groove, wherein the distal ring includes a distal groove, wherein a portion of the one or more patches is positioned in the proximal groove, wherein another portion of the one or more patches is positioned in the distal groove, and wherein a distal portion of the one or more actuation elements is positioned within the distal groove.

19. A medical device, comprising:

a handle, wherein the handle includes one or more actuators;

an end cap configured to be coupled to a distal end of another medical device, wherein the end cap includes:

a proximal ring including a proximal groove, a distal ring including a distal groove, and a body portion between the proximal ring and the distal ring;

one or more patches, wherein the one or more patches are coupled to the end cap such that a portion of each of the one or more patches is positioned within the proximal groove, and such that another portion of each of the one or more patches is positioned within the distal groove; and one or more actuation elements, wherein the one or more actuation elements extend from the one or more actuators to a position between a portion of the one or more patches and the body portion of the end cap, wherein a distal portion of each of the one or more actuation elements is positioned within the distal groove, and wherein movement of the one or more actuators at least partially deploys the one or more patches from the end cap.

20. The medical device of claim 19, wherein the one or more actuators are one or more secondary actuators, and wherein the handle further includes a primary actuator configured to control the position of the end cap relative to the distal end of the another medical device, and wherein the one or more secondary actuators are movable within respective channels formed by one or more wings in the primary actuator.

* * * * *